United States Patent [19]

Winston et al.

[11] Patent Number: 4,599,217

[45] Date of Patent: Jul. 8, 1986

[54] CORROSION SIMULATOR USEFUL FOR HEAT EXCHANGERS CONDENSING VAPORS CONTAINING WATER AND METHOD FOR USING SAME

[75] Inventors: William G. Winston, Houston; David M. Groves, Huffman, both of Tex.

[73] Assignee: Exxon Chemical Patents Inc., Florham Park, N.J.

[21] Appl. No.: 693,635

[22] Filed: Jan. 22, 1985

[51] Int. Cl.$^4$ .............................. G01N 17/00
[52] U.S. Cl. ................. 422/53; 73/432 SD; 203/7; 422/62; 436/6
[58] Field of Search .............. 422/53, 62; 73/432 SD, 73/61.2; 436/6, 55; 203/7

[56] References Cited

U.S. PATENT DOCUMENTS

| | | | |
|---|---|---|---|
| 3,649,167 | 3/1972 | Sawyer | 73/863.12 X |
| 4,160,948 | 7/1979 | Tytgat et al. | 436/6 X |
| 4,226,693 | 10/1980 | Maes | 422/53 X |
| 4,335,072 | 6/1982 | Barnett et al. | 422/53 |

*Primary Examiner*—Robert Lindsay
*Attorney, Agent, or Firm*—R. A. Dexter; R. L. Graham

[57] ABSTRACT

Apparatus for determining the corrosion rate of industrial condensing equipment so that corrosion inhibitors may be effectively utilized to control corrosion. The apparatus which simulates a cooling circuit for process streams which require the introduction of reagents to inhibit corrosion includes a primary condenser with automatic cooling control and more than one serially connected cooling-monitoring section, associated means for monitoring corrosion rate, temperature, and/or dewpoint and means for adjustably controlling the process stream cooling rate of said cooling-monitoring sections. The process stream is flowed through said serial connected cooling-monitoring sections in order to cool the vapors in a manner which simulates cooling that will take place in a parallel connected heat exchanger unit. The monitoring means which include corrosion and temperature probes and dew point measuring units provide monitoring means to determine corrosion rates at the various temperature levels of the hydrocarbons so that a corrosion profile can be established and related to the temperature of the vapors at various locations in the heat exchange units of the equipment.

12 Claims, 3 Drawing Figures

CORROSION SIMULATOR USEFUL FOR HEAT EXCHANGERS CONDENSING VAPORS CONTAINING WATER AND METHOD FOR USING SAME

INTRODUCTION

This invention relates in general to an apparatus that will determine corrosion rates in vapor condensing systems when one of the components of the vapor is water or some other fluid with sufficient ionic strength to promote corrosion. This apparatus will profile corrosion versus temperature in a condensing system and can be used to evaluate the effectiveness of corrosion inhibitors in controlling this corrosion.

BACKGROUND OF THE INVENTION

Refinery and petrochemical plants have many processes where hydrocarbon containing various amounts of water is heated to vapor and, later in the process, is condensed back to a liquid state. Many of these process contain or generate one or more corrosive components. These corrosive components may include strong acids such as hydrochloric, sulfuric, or phosphoric acid and/or weak acids such as hydrogen sulfide, carbon dioxide, and organic acids. When the vapors in these units condense, water containing one or more corrosives attacks the internal surfaces of the condensing sections. The exact point where corrosion begins, the nature, and the severity of the corrosion attack cannot be predicted accurately without making actual measurements.

Heretofore, a number of devices and techniques have been used to monitor corrosion, but the accuracy of these devices and techniques has been limited. For example, ultrasonic equipment has been used to measure with sound waves the metal thickness of equipment. This method is limited because the corrosion process is often localized to only a portion of the equipment and this area can be missed in testing or isolated to an area that is inaccessible to testing.

Weight loss coupons have been used to detect and measure corrosion in these units. The corrosion rates determined from the use of a coupon only represents the time weighted average of corrosion that occurred at the point of the coupon's installation. In order to predict the corrosion rate of a refinery or petrochemical unit, it is known that the most severe corrosion will occur at a point at or near the point of initial water condensation referred to as the dew point. In this equipment, it has been learned that this point is most typically inside a heat exchanger or a condenser. This area of highest corrosion inside a heat exchanger can be shifted as the unit's vapor temperature and pressure shifts and both the location and the shifting of the corrosion makes it impossible to maintain a coupon in this area.

Electrical resistance probes are considered to be the most accurate device to monitor refinery and petrochemical equipment corrosion and these devices are superior to corrosion coupons as the time weighting factor can be greatly reduced to measure changes in corrosion rates over a much shorter interval. The electrical resistance probes do, however, share the weakness with corrosion coupons of limited access and a shifting corrosion pattern.

Sampling the process stream followed by chemical testing for corrosive agents and corrosion by-products has proven useful in estimating corrosion. These techniques, however, do not yield much useful information on the area or type of corrosion and the sensitivity is poor.

There is an apparatus for measuring corrosion potential which analyzes the initial condensate condition where the temperature of the surrounding environment reaches the dew point of water, as disclosed in U.S. Pat. No. 3,649,167. However this system will not indicate metal loss or corrosion activity.

It is also known that there is an apparatus which includes a water box having a coil arranged in the box through which hydrocarbon vapors are directed. Cooling water is forced through the box in a counterflow direction to cool the vapor and simulate the cooling that will take place in heat exchanger units. Corrosion and temperature probes are arranged along the coil to determine the corrosion rates at various temperature levels of the hydrocarbon. This device is disclosed in U.S. Pat. No. 4,335,072. However, this system has several restrictive limitations. The unit must be set to only one temperature by adjusting the cooling water flow and/or process flow. The temperature profile established is both uncontrollably fixed and individually unadjustable. The cooling water box imposes strict limits on the volume of process flow required and the amount of temperature change desired. This unit also has no rapid or accurate method to determine the process flow dew point which identifies the critical temperature range for profiling corrosion.

OBJECT OF THE INVENTION

It is therefore an object of the present invention to provide a new and improved apparatus to quickly and accurately measure corrosion rates as a function of temperature in vapor condensing equipment in order to promptly and effectively control this corrosion.

Another object of the present invention is the provision of a corrosion simulator for vapor condensing systems to simulate the corrosion environment present on condenser or heat exchanger surfaces used in the equipment.

Another object of the present invention resides in the provision of a corrosion simulator of a vapor condensing system that is capable of measuring corrosion occurring on the internal metal surfaces of condensers or heat exchanger units, of measuring the temperature at the same locations of the process flow, and of measuring the fluid conductance to detect the initial liquid water condensation at the same location.

A still further object of the present invention of a corrosion simulator for vapor condensing systems is the capability to automatically and continuously control the initial temperature in this device and the capability to adjust the temperature profile manually at several points past the automatic control.

SUMMARY OF THE INVENTION

The above objects have been met by the discovery that the corrosion occurring in equipment condensing water from a hydrocarbon process stream containing water vapor can be dynamically simulated by a cooling circuit which flows a parallel branch of said process stream through more than one, preferably 4 to 8 (optimally 6), serially connected cooling-monitoring sections.

In addition, this invention has electrical probes in the monitoring sections which are capable of measuring fluid conductance which meet the object of the invention in being able to identify the point where the initial water condenses, more commonly known as the dew point.

BRIEF DESCRIPTION OF THE DRAWING

Other objects, features, and advantages of the invention will be apparent from the following detailed disclosure, taken in conjunction with the accompanying sheets of drawings, wherein like reference numerals refer to like parts, in which.

DETAILED DESCRIPTION OF THE INVENTION

Figure 1:
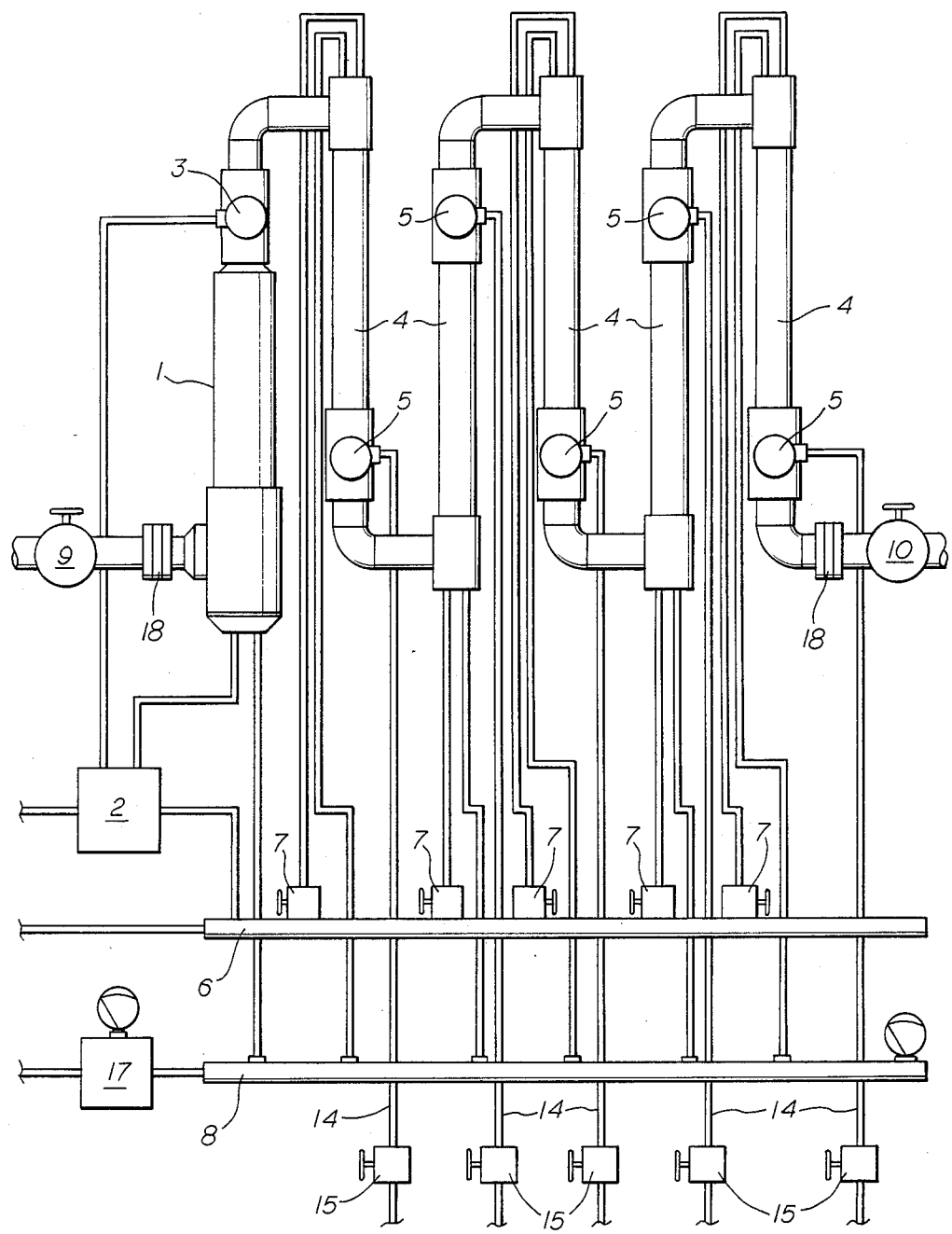
FIG. 1 is a diagrammatic view of the Refinery Corrosion Monitor of the invention.

Referring now to FIG. 1, the Refinery Corrosion Monitor (hereafter defined as RCM) is shown as it would be connected to a vapor condensing system for monitoring and optimizing a corrosion control program used in industrial vapor condensing equipment. The RCM begins vapor processing with an oversized initial condenser 1, an automatic control valve 2 and an automatic control sensor section 3. Following is a series of one to seven, optimally five standard condensers 4 and monitoring sections 5. The cooling water is supplied to the condensers from the cooling water manifold 6. The amount of cooling is controlled by the automatic control valve 2 and the manually operated valves 7. The cooling water leaves the RCM through the cooling water outlet manifold 8.

Figure 2:
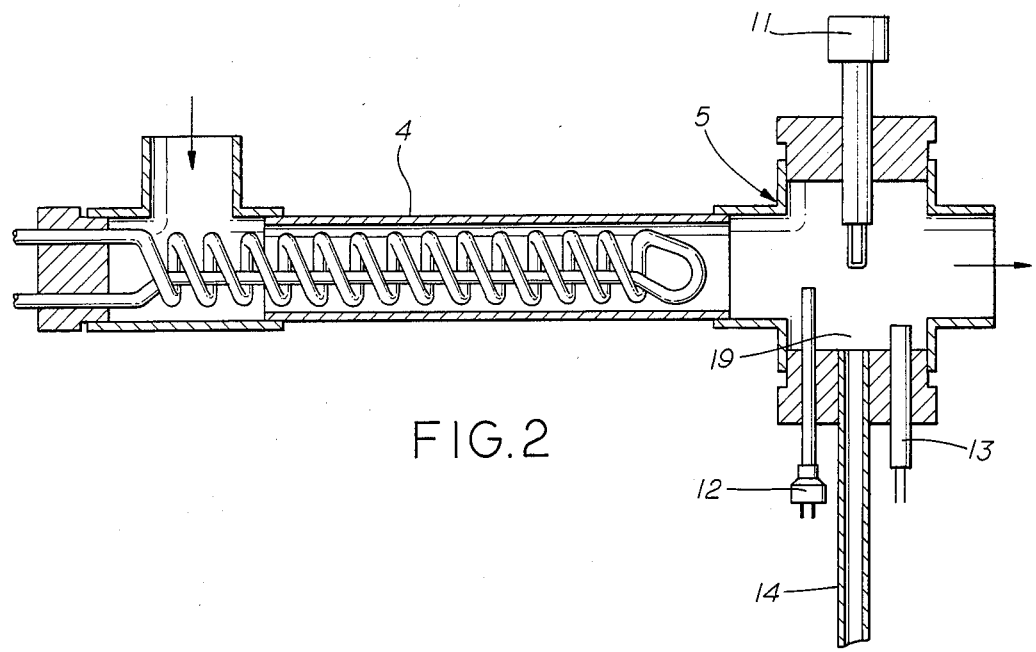
FIG. 2 is a cross-sectional view of the condenser and monitoring sections of the Refinery Corrosion Monitor.
Figure 3:
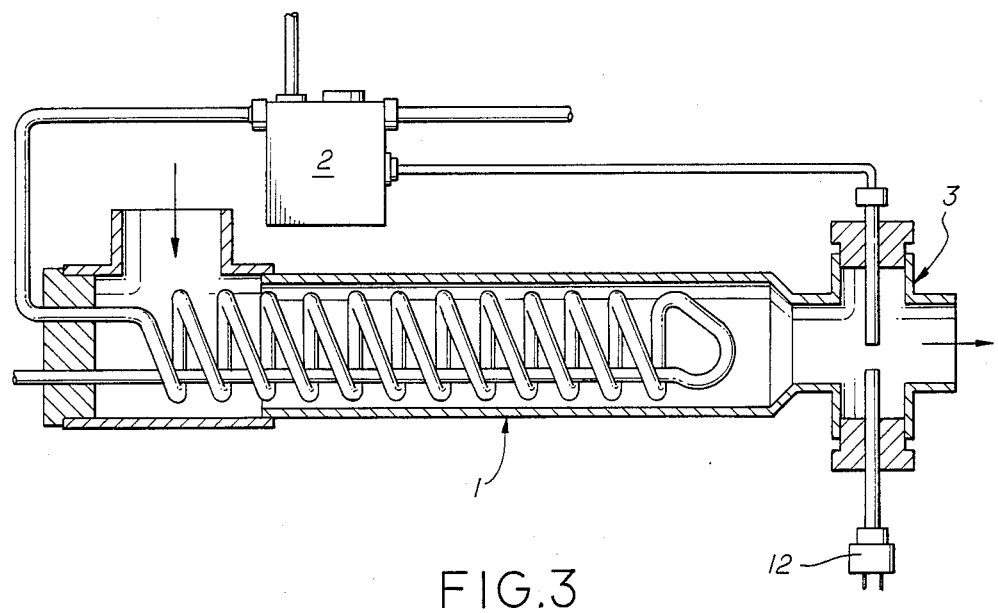
FIG. 3 is a cross-sectional view of the Refinery Corrosion Monitor's oversized initial condenser with an automatic temperature controller.

The RCM simulates a vapor condensing system in the following manner. A sidestream from a vapor condensing system is supplied to the RCM through suitable piping to the process inlet valve 9. The temperature of the sidestream should be at least 5° C. but less than 40° C. above the point where water in the system will begin to condense. The sidestream is initially cooled and the temperature is controlled in the initial oversized condenser 1. The temperature control is accomplished by use of an automatic control valve 2 that adjusts to vary the cooling water flow to the oversized condenser 1. The automatic control valve 2 responds to a temperature signal from a temperature sensor 3 in the sidestream flow out of condensor 1. A thermocouple located adjacent to the temperature sensor 3 and also in the sidestream flow is available to verify the temperature control. The control valve 2 should provide a constant temperature of at least ±4° C., preferably ±2° C., of the sidestream vapor exiting condenser 1. The following standard condensers 4 are used to profile the vapor condensation. The temperatures are established at the desired points as indicated by subsequent thermocouples (as shown in FIG. 2) by manually setting the cooling water flow with the standard condenser manually operated control valves 7. The sidestream flow leaves the RCM from the sidestream outlet valve 10 to return to the process equipment at a point with sufficient pressure drop (at least 10 psi) to insure good flow through the RCM.

The monitoring station shown in FIG. 2 performs several functions. The station includes a corrosion probe 11, a thermocouple 12, a conductance probe 13, and a sample line 14. The corrosion probe 11 can be any suitable electronic corrosion measuring instrument or any type of corrosion coupon, or a combination of an electronic probe and a corrosion coupon. The preferred probe is the Corrosometer type electrical resistance probe. The thermocouple 12 can be of any suitable type matched to the temperature and pressure range of equipment to be simulated. The thermocouple probe 12 should be constructed of a suitable material to resist the corrosives of the condensed fluid of the equipment being simulated. The conductance probe 13 is a device capable of measuring the conductance of condensed fluids. This is accomplished by having two or more electrically isolated, corrosioninert points connected to suitable external wires which would allow the conductance across the two points to be measured with any commercially available conductance or resistance measuring instrument. If a resistance measuring instrument is used, it should be noted that the conductance value is the reciprocal of the resistance value. The sample lines 14 are connected to the monitoring station in a small line indentation. The sample lines 14 are operated by use of associated external valve 15 as seen in FIG. 1. The sample lines 14 provide a means to remove condensed fluids at each of the monitoring stations. Typically, the condensed fluid samples would be collected for analysis of the water portion for information about the corrosion potential or the occurrence of corrosion. This information can include pH, chloride concentration, iron concentration, and other data known to be relevant to corrosion and potential for corrosion.

The RCM is advantageously compact and portable with typical dimensions of less than or equal to 4 ft by 3 ft by 1½ ft with a weight less than 200 lbs.

The RCM should be placed in a easily accessible area for service, but its size and weight allows placement on most elevated platforms common to vapor condensing systems. For full operation, the RCM utilizes a commonly available water source such as file water or cooling tower water. Positive water pressure of 20–50 psi is needed for operation. A commercial water pressure regulator or a booster pump can be used to supply constant water pressure in the required pressure range. A back pressure regulator 17 is used on the cooling water outlet manifold 8 to elevate the cooling water boiling point and thus prevent evaporation and the resulting solids fouling of the cooling coil. The RCM requires industrial compressed gas—air or nitrogen—at 50 psi. The gas is used to provide the opposing force in the back pressure regulator 17 and to power the automatic control valve 2.

The unit is designed to incline slightly from inlet gate 9 to outlet gate 10 when placed on a flat surface. This incline (typically 5°) is to provide condensate drainage through the unit. The RCM is equipped with industrial quality gate valves at 9 and 10. The valves provide the means to isolate the RCM so that service requiring opening the RCM can be done. In addition, there are flange connectors 18 so that the RCM can be disconnected from the process independently of the process operations.

An external case is provided to insulate the RCM from adverse weather conditions. The case is made of insulated panels, preferrably aluminum with fire proof insulating inserts. The panels are attached externally for easy removal.

The case has two ports: a top service port which provides access to the corrosion probes 11, thermocouples 12, automatic control valve 2, and the conductance probes 13; and, a side access port for access to the manually actuated standard condenser control valves 7 and the sample line valves 15.

The process piping of FIG. 1 which includes all piping exposed to process flow from the process inlet valve 9 to the process outlet valve 10 can be constructed of any suitable material recommended for the process stream being evaluated. A typical construction is of Schedule 40 (or better) malleable iron pipe and fittings. Since the condenser coils of the condensers are the coolest metal surfaces in the RCM and, therefore, exposed to the harshest corrosion conditions, these coils should be constructed of corrosion resistant metal such monel or stainless steel. The water line and water manifold is constructed of suitable tubing, piping, and fittings, typically copper or steel. The typical RCM is constructed of $1\frac{1}{2}$ inch malleable iron pipe and fittings with $2\frac{1}{2}$ to 3 inch malleable iron pipe and fittings for the oversized condenser. The tubing size for the water lines and condenser coils is typically $\frac{1}{4}$ to $\frac{1}{2}$ inch diameter. The condenser coil length of the standard coils is between 3 and 10 feet, typically 6 feet in length, fashioned into a $1\frac{1}{4}$–$1\frac{1}{2}$ inch diameter coil. The oversized condenser coil is 6–14 feet in length, typically 10 feet, fashioned into a $2\frac{1}{2}$–3 inch diameter coil.

In a vapor condensing system, the most severe point of corrosion attack is at a region where water is initially condensed. This point of severe corrosion changes inside condensing equipment as the temperature, pressure, and/or composition of the vapor change. In addition the accuracy of the control equipment can cause the location of severe corrosion to shift. Conventional corrosion probes such as electric resistance type or coupon probes can only be placed in limited areas in the condensing process. The most typical locations for corrosion probes are at the inlet or outlet of a condenser or heat exchanger. A combination of the limited access and the shifting corrosion pattern results in a high percentage of these probes yielding poor or marginal information on corrosion. Other simulators such as noted in U.S. Pat. No. 4,335,072 overcome the problem of probe placement but lack the automatic process temperature control. This invention with the automatic process temperature control continuously corrects the side stream temperature to a constant value. By holding the temperature constant, the corrosion profile of a condensing stream is more constant and a corrosion profile can be determined more quickly and with more distinction. With the temperature variably controlled the effects of pressure and vapor composition will be easier to identify and quantify. The simulator's downstream condensers, having independent and adjustable cooling water feed, provide another unique advantage to this invention. The flexibility of individual control allows monitoring a corrosion profile over any temperature range from very small, typically five corrosion readings over 10° C., to very large, typically five corrosion readings over 50° C. This fact allows this invention to either model a single condenser in a series or a whole series of condensers.

The monitoring sections of this invention contain the corrosion probe, typically a Corrosometer of the type manufactured by Rohrback Instruments of Santa Fe Springs, Calif., a thermocouple, a sample line, and a conductance probe. The close placement of the thermocouple to the corrosion probe allows accurate correlation of corrosion rate to temperature. The conductance probe is useful because of the fact that there is a large conductance difference between vapor or hydrocarbon liquids and water, even water with very low ionic strength. Mixtures of hydrocarbon and water show a large difference in conductance as compared to hydrocarbon with no water. The conductance probe, in practice, will detect the initial condensation of water and this information can be used to correlate temperature, corrosion, and the initial condensation. In addition, as this initial condensation can be detected easily and quickly, the conductance probes will be useful in determining the most corrosive temperature when setting up a corrosiontemperature profile. The sample lines 14 are used to withdraw process samples for later chemical analysis. This sample system is unique to this invention in that the sample line 14 as seen in FIG. 2 enters the monitoring section into a reservoir 19 that will contain no more than 5–20 milliliters volume, preferably 10. This reservoir 19 is intended to trap small fluid samples but to provide only minimal retention time to minimize the establishment of artificial equilibrium between liquid and vapor phases. The sample lines 14 are of a small diameter ($\frac{1}{8}$ to $\frac{1}{4}$ inch) to provide for easy purging before collection of fresh condensate samples.

The apparatus of the invention thus provides a novel and useful method for simulating the corrosion point and/or rate in equipment condensing vapors containing water which involves the steps of diverting a portion of said vapors immediately prior to its entry into said equipment, flowing said diverted portion through at least two, usefully four to eight, serially connected cooling-monitoring means and measuring the temperature and/or conductivity at at least two of said means whereby the definition of the rate and/or location of corrosion occurring on the internal metal surfaces of said equipment can be precisely defined. This method can also include the steps of adjusting the cooling rate of the cooling-monitoring means and/or recovering a sample of said portion passing through each of said means in order to better simulate the internal corrosion profile within the equipment.

Clearly the apparatus and method of the invention also provide a method of reducing corrosion occurring on the internal metal surfaces of equipment condensing vapors containing water utilizing the steps of diverting a portion of said vapors immediately prior to its entry into said equipment, flowing said diverted portion through at least two serially connected cooling-monitoring means, measuring the temperature and/or conductivity at at least two of said means, plotting the data from said measuring to define the existence and location of at least one dew point within said equipment and introducing at least a corrosion inhibiting amount (such as an amount sufficient to provide a pH of greater than 5, generally above 6) or to provide a corrosion inhibitor film on metal surfaces of a corrosion inhibitor into said location within said equipment.

The invention clearly provides a method for altering the condensation conditions of equipment condensing water vapors to shift the location of the dew point to a region within the equipment having a lower potential for corrosion resulting from water condensation.

Since it is now possible to determine the location, which location(s) can be shifted as required, it is possible to introduce the corrosion inhibitor into a region(s) immediate to the dew point(s) with attendant reduction in the amount of chemical required for inhibition.

What is claimed is:

1. In industrial equipment having a vapor line to condensing and/or heat exchange equipment, a corrosion simulator for simulating and measuring the corrosion activity on the internal surfaces of said equipment, said simulator comprising more than one serially connected cooling-monitoring sections and associated with each thereof, means for monitoring corrosion rate and means for independently adjustably controlling the process stream cooling rate of each of said cooling-monitoring sections wherein the first of said serially connected cooling-monitoring sections has means to automatically control the temperature of the process stream therein.

2. The simulator defined in claim 1, which further includes a temperature probe at each corrosion monitoring means for measuring the temperature at the corrosion probe and provide a temperature-corrosion profile for the condensing and/or heat exchange equipment.

3. The simulator defined in claim 1, which further includes a sampling line at at least one corrosion monitoring means for taking a liquid sample to analysis.

4. The simulator defined in claim 3, which includes a reservoir for each said sampling line designed to provide a liquid sample that is in natural equilibrium as would be found in the process being simulated.

5. The simulator defined in claim 1 which further includes means to determine the point at which water begins to condense as a means to predict the temperature range where corrosion is most intense.

6. A method for simulating the corrosion point and/or rate in equipment condensing vapors containing water comprising the steps of diverting a portion of said vapors immediately prior to its entry into said equipment, flowing said diverted portion through at least two serially connected cooling-monitoring means, independently adjusting the cooling rate of each of said means in order to better simulate the internal corrosion profile within said equipment and measuring the temperature and/or conductivity at at least two of said means whereby the definition of the rate and/or location of corrosion occurring on the internal metal surfaces of said equipment can be precisely defined.

7. The simulator defined in claim 2, which further includes a sampling line at at least one corrosion monitoring-means for taking a liquid sample to analysis.

8. The method according to claim 6 wherein there is included the step of recovering a sample of said portion passing through each of said means.

9. A method of reducing corrosion occurring on the internal metal surfaces of equipment condensing vapors containing water comprising the steps of diverting a portion of said vapors immediately prior to its entry into said equipment, flowing said diverted portion through at least two serially connected cooling-monitoring means, measuring the temperature and/or conductivity at at least two of said means, plotting the data from said measuring to define the existence and location of at least one dew point within said equipment and introducing at least a corrosion inhibiting amount of a corrosion inhibitor into said location within said equipment.

10. A method according to claim 9 comprising the additional step of altering the condensation conditions of said equipment whereby the location of said dew point is moved to a region of lower potential for corrosion resulting from water condensation.

11. The simulator defined in claim 7 which includes a reservoir for each said sampling line designed to provide a liquid sample that is in natural equilibrium as would be found in the process being simulated.

12. The simulator defined in claim 11 which further includes means to determine the point at which water begins to condense as a means to predict the temperature range where corrosion is most intense.

* * * * *